(12) United States Patent
Muller et al.

(10) Patent No.: US 9,044,308 B2
(45) Date of Patent: Jun. 2, 2015

(54) SYSTEMS AND METHODS FOR RESHAPING AN EYE FEATURE

(75) Inventors: David Muller, Boston, MA (US); Vance Thompson, Sioux Falls, SD (US)

(73) Assignee: Avedro, Inc., Waltham, MA (US)

( * ) Notice: Subject to any disclaimer, the term of this patent is extended or adjusted under 35 U.S.C. 154(b) by 0 days.

(21) Appl. No.: 13/480,127

(22) Filed: May 24, 2012

(65) Prior Publication Data

US 2012/0303008 A1   Nov. 29, 2012

Related U.S. Application Data

(60) Provisional application No. 61/489,554, filed on May 24, 2011, provisional application No. 61/492,499, filed on Jun. 2, 2011.

(51) Int. Cl.
*A61B 18/18* (2006.01)
*A61F 9/013* (2006.01)
*A61F 9/008* (2006.01)

(52) U.S. Cl.
CPC .............. *A61F 9/013* (2013.01); *A61F 9/00804* (2013.01); *A61F 9/00836* (2013.01); *A61F 2009/00853* (2013.01); *A61F 2009/00872* (2013.01)

(58) Field of Classification Search
CPC .................................................. A61F 9/00804
USPC ......................................................... 606/4–6
See application file for complete search history.

(56) References Cited

U.S. PATENT DOCUMENTS

| 4,034,750 A | 7/1977 | Seiderman |
| 4,161,013 A | 7/1979 | Grodzinsky et al. |

(Continued)

FOREIGN PATENT DOCUMENTS

| DE | 10 2008 04683 | 3/2010 |
| EP | 1 561 440 A1 | 8/2005 |

(Continued)

OTHER PUBLICATIONS

Kanellopoulos, Anastasios John; "Collagen Cross-linking in Early Keratoconus With Riboflavin in a Femtosecond Laser-created Pocket: Initial Clinical Results", Journal of Refractive Surgery, Aug. 18, 2009.*

(Continued)

*Primary Examiner* — William Thomson
*Assistant Examiner* — John R Downey
(74) *Attorney, Agent, or Firm* — McDonnell Boehnen Hulbert & Berghoff LLP

(57) ABSTRACT

Systems and methods include a cutting instrument that creates incisions in selected areas of the cornea; an eye therapy system that applies reshaping forces to the cornea; and a controller that determines the selected areas of the cornea for the incisions and the reshaping forces from the eye therapy system, such that the reshaping forces and the incisions combine to achieve corrective reshaping of the cornea. Other systems and methods include measuring an eye to determine a required amount of reshaping of a cornea; determining one or more doses of cross-linking agent and one or more corresponding doses of photoactivating light according to the required amount of reshaping; applying the cross-linking agent to the cornea; and delivering, from a light source, the photoactivating light to the area of the eye, the photoactivating light combining with the cross-linking agent to induce the corrective reshaping of the cornea.

23 Claims, 5 Drawing Sheets

(56) References Cited

U.S. PATENT DOCUMENTS

| | | |
|---|---|---|
| 4,326,529 A | 4/1982 | Doss et al. |
| 4,381,007 A | 4/1983 | Doss |
| 4,665,913 A | 5/1987 | L'Esperance, Jr. et al. |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,969,912 A | 11/1990 | Kelman et al. |
| 4,994,058 A | 2/1991 | Raven et al. |
| 5,016,615 A | 5/1991 | Driller et al. |
| 5,019,074 A | 5/1991 | Muller |
| 5,103,005 A | 4/1992 | Gyure et al. |
| 5,171,254 A | 12/1992 | Sher |
| 5,171,318 A | 12/1992 | Gibson et al. |
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,618,284 A | 4/1997 | Sand |
| 5,624,437 A | 4/1997 | Freeman et al. |
| 5,634,921 A | 6/1997 | Hood et al. |
| 5,766,171 A | 6/1998 | Silvestrini |
| 5,779,696 A | 7/1998 | Berry et al. |
| 5,786,893 A | 7/1998 | Fink et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,099,521 A | 8/2000 | Shadduck |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,188,500 B1 | 2/2001 | Rudeen et al. |
| 6,218,360 B1 | 4/2001 | Cintron et al. |
| 6,223,075 B1 | 4/2001 | Beck et al. |
| 6,270,221 B1 | 8/2001 | Liang et al. |
| 6,293,938 B1 | 9/2001 | Muller et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,334,074 B1 | 12/2001 | Spertell |
| 6,342,053 B1 | 1/2002 | Berry |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,572,849 B2 | 6/2003 | Shahinian, Jr. |
| 6,617,963 B1 | 9/2003 | Watters et al. |
| 6,673,067 B1 | 1/2004 | Peyman |
| 6,918,904 B1 | 7/2005 | Peyman |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,270,658 B2 | 9/2007 | Woloszko et al. |
| 7,331,350 B2 | 2/2008 | Kochevar et al. |
| 7,402,562 B2 | 7/2008 | DeWoolfson et al. |
| 7,753,943 B2 | 7/2010 | Strong |
| 7,898,656 B2 | 3/2011 | Yun et al. |
| 7,935,058 B2 | 5/2011 | Dupps et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 2001/0041856 A1 | 11/2001 | McDaniel |
| 2001/0055095 A1 | 12/2001 | D'Souza et al. |
| 2002/0002369 A1 | 1/2002 | Hood |
| 2002/0013577 A1 | 1/2002 | Frey et al. |
| 2002/0049437 A1 | 4/2002 | Silvestrini |
| 2002/0099363 A1 | 7/2002 | Woodward et al. |
| 2002/0159618 A1 | 10/2002 | Freeman et al. |
| 2002/0164379 A1 | 11/2002 | Nishihara et al. |
| 2003/0018255 A1 | 1/2003 | Martin et al. |
| 2003/0175259 A1 | 9/2003 | Karageozian et al. |
| 2003/0189689 A1 | 10/2003 | Rathjen |
| 2003/0216728 A1 | 11/2003 | Stern et al. |
| 2003/0231285 A1 | 12/2003 | Ferguson |
| 2004/0001821 A1 | 1/2004 | Silver et al. |
| 2004/0002694 A1 | 1/2004 | Pawlowski et al. |
| 2004/0071778 A1 | 4/2004 | Bellmann et al. |
| 2004/0093046 A1 | 5/2004 | Sand |
| 2004/0111086 A1 | 6/2004 | Trembly et al. |
| 2004/0143250 A1 | 7/2004 | Trembly |
| 2004/0199079 A1 | 10/2004 | Chuck et al. |
| 2004/0199158 A1 | 10/2004 | Hood et al. |
| 2004/0204707 A1 | 10/2004 | Hood et al. |
| 2004/0243160 A1 | 12/2004 | Shiuey et al. |
| 2005/0038471 A1 | 2/2005 | Chan et al. |
| 2005/0096515 A1 | 5/2005 | Geng |
| 2005/0149006 A1* | 7/2005 | Peyman .................... 606/5 |
| 2005/0271590 A1 | 12/2005 | Schwartz et al. |
| 2006/0135957 A1* | 6/2006 | Panescu ................... 606/41 |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0195076 A1 | 8/2006 | Blumenkranz et al. |
| 2006/0276777 A1 | 12/2006 | Coroneo |
| 2006/0287662 A1 | 12/2006 | Berry et al. |
| 2007/0024860 A1 | 2/2007 | Tobiason et al. |
| 2007/0027509 A1 | 2/2007 | Eisenberg et al. |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203547 A1 | 8/2007 | Costello et al. |
| 2007/0244470 A1 | 10/2007 | Barker et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0116096 A1 | 5/2009 | Zalevsky et al. |
| 2009/0130176 A1 | 5/2009 | Bossy-Nobs et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0234335 A1 | 9/2009 | Yee |
| 2009/0271155 A1 | 10/2009 | Dupps et al. |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | De Juan, Jr. et al. |
| 2010/0057060 A1 | 3/2010 | Herekar |
| 2010/0069894 A1* | 3/2010 | Mrochen et al. ............. 606/4 |
| 2010/0082018 A1 | 4/2010 | Panthakey |
| 2010/0094197 A1 | 4/2010 | Marshall et al. |
| 2010/0114109 A1 | 5/2010 | Peyman |

(56) References Cited

U.S. PATENT DOCUMENTS

| | | | |
|---|---|---|---|
| 2010/0149487 A1 | 6/2010 | Ribak | |
| 2010/0149842 A1 | 6/2010 | Muller et al. | |
| 2010/0173019 A1 | 7/2010 | Paik et al. | |
| 2010/0189817 A1 | 7/2010 | Krueger et al. | |
| 2010/0191228 A1* | 7/2010 | Ruiz et al. | 606/5 |
| 2010/0203103 A1 | 8/2010 | Dana et al. | |
| 2010/0204584 A1 | 8/2010 | Ornberg et al. | |
| 2010/0210996 A1 | 8/2010 | Peyman | |
| 2010/0286156 A1 | 11/2010 | Pinelli | |
| 2010/0318017 A1 | 12/2010 | Lewis et al. | |
| 2011/0077624 A1 | 3/2011 | Brady et al. | |
| 2011/0098790 A1 | 4/2011 | Daxer | |
| 2011/0118654 A1 | 5/2011 | Muller et al. | |
| 2011/0152219 A1 | 6/2011 | Stagni et al. | |
| 2011/0190742 A1 | 8/2011 | Anisimov | |
| 2011/0202114 A1 | 8/2011 | Kessel et al. | |
| 2011/0208300 A1 | 8/2011 | de Juan, Jr. et al. | |
| 2011/0237999 A1 | 9/2011 | Muller et al. | |
| 2011/0264082 A1 | 10/2011 | Mrochen et al. | |
| 2011/0288466 A1 | 11/2011 | Muller et al. | |
| 2011/0301524 A1 | 12/2011 | Bueler et al. | |
| 2012/0083772 A1 | 4/2012 | Rubinfeld et al. | |
| 2012/0203051 A1 | 8/2012 | Brooks et al. | |
| 2012/0203161 A1 | 8/2012 | Herekar | |
| 2012/0215155 A1 | 8/2012 | Muller et al. | |
| 2012/0283621 A1 | 11/2012 | Muller et al. | |
| 2012/0289886 A1 | 11/2012 | Muller et al. | |
| 2012/0302862 A1 | 11/2012 | Yun et al. | |
| 2012/0310083 A1 | 12/2012 | Friedman et al. | |
| 2012/0310223 A1 | 12/2012 | Knox et al. | |
| 2013/0060187 A1 | 3/2013 | Friedman et al. | |
| 2013/0085370 A1 | 4/2013 | Friedman et al. | |
| 2013/0116757 A1 | 5/2013 | Russmann | |
| 2014/0194957 A1 | 7/2014 | Rubinfield et al. | |
| 2014/0249509 A1 | 9/2014 | Rubinfield et al. | |

FOREIGN PATENT DOCUMENTS

| | | | | |
|---|---|---|---|---|
| EP | 1 790 383 A1 | | 5/2007 | |
| EP | 2 253 321 A1 | | 11/2010 | |
| EP | 2 490 621 | | 8/2012 | |
| IT | MI2010A001236 | | 5/2010 | |
| KG | 1376 | | 8/2011 | |
| RU | 2086215 | | 8/1997 | |
| RU | 2098057 | | 12/1997 | |
| RU | 2121825 | | 11/1998 | |
| RU | 2127099 | | 3/1999 | |
| RU | 2127100 | | 3/1999 | |
| RU | 2309713 | | 11/2007 | |
| RU | 2359716 | | 6/2009 | |
| RU | 2420330 | | 6/2011 | |
| RU | 2428152 | | 9/2011 | |
| RU | 2456971 | | 7/2012 | |
| WO | WO 00/74648 A2 | | 12/2000 | |
| WO | WO 01/58495 | | 8/2001 | |
| WO | WO 2004/052223 A2 | | 6/2004 | |
| WO | WO 2005/110397 A1 | | 11/2005 | |
| WO | WO 2006/012947 A2 | | 2/2006 | |
| WO | WO 2006/128038 A2 | | 11/2006 | |
| WO | WO 2007/001926 A2 | | 1/2007 | |
| WO | WO 2007/053826 | | 5/2007 | |
| WO | WO 2007/081750 | | 7/2007 | |
| WO | WO 2007/120457 A2 | | 10/2007 | |
| WO | WO 2007/139927 | | 12/2007 | |
| WO | WO 2007/143111 | | 12/2007 | |
| WO | WO 2008/000478 A1 | | 1/2008 | |
| WO | WO 2008/052081 | | 5/2008 | |
| WO | WO 2008/095075 | | 8/2008 | |
| WO | WO 2009/114513 | * | 3/2009 | A61K 33/40 |
| WO | WO 2009/073213 | | 6/2009 | |
| WO | WO 2009/114513 | | 9/2009 | |
| WO | WO 2009/146151 | | 12/2009 | |
| WO | WO 2010/011119 A1 | | 1/2010 | |
| WO | WO 2010/015255 | | 2/2010 | |
| WO | WO 2010/023705 A1 | | 3/2010 | |
| WO | WO 2010/093908 | | 8/2010 | |
| WO | WO 2011/019940 | | 2/2011 | |
| WO | WO 2011/116306 | | 9/2011 | |
| WO | WO 2012/004726 | | 1/2012 | |
| WO | WO 2012/149570 | | 11/2012 | |
| WO | WO 2012/174453 | | 12/2012 | |
| WO | WO 2012/047307 | | 4/2013 | |
| WO | WO 2013/148713 | | 10/2013 | |
| WO | WO 2013/148895 | | 10/2013 | |
| WO | WO 2013/148896 | | 10/2013 | |
| WO | WO 2013/149075 | | 10/2013 | |
| WO | WO 2014/202736 | | 12/2014 | |

OTHER PUBLICATIONS

Acosta A. et al., "Corneal Stroma Regeneration in Felines After Supradescemetic Keratoprothesis Implantation," *Cornea*, vol. 25, No. 7, pp. 830-838; Aug. 2006 (9 pages).

Baier J. et al., "Singlet Oxygen Generation by UVA Light Exposure of Endogenous Photosensitizers," *Biophysical Journal*, vol. 91(4), pp. 1452-1459; Aug. 15, 2006 (8 pages).

Berjano E., et al., "Radio-Frequency Heating of the Cornea: Theoretical Model and In Vitro Experiments," *IEEE Transactions on Biomedical Engineering*, vol. 49, No. 3, pp. 196-205; Mar. 2002 (10 pages).

Berjano E., et al., "Ring Electrode for Radio-frequency Heating of the Cornea: Modelling and in vitro Experiments," *Medical & Biological Engineering & Computing*, vol. 41, pp. 630-639; Jun. 2003 (10 pages).

Chan B.P., et al., "Effects of photochemical crosslinking on the microstructure of collagen and a feasibility study on controlled protein release;" *Acta Biomaterialia*, vol. 4, Issue 6, pp. 1627-1636; Jul. 1, 2008 (10 pages).

Chandonnet, "CO2 Laser Annular Thermokeratoplasty: A Preliminary Study," *Lasers in Surgery and Medicine*, vol. 12, pp. 264-273; 1992 (10 pages).

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).

Corbett M., et al., "Effect of Collagenase Inhibitors on Corneal Haze after PRK," *Exp. Eye Res.*, vol. 72, Issue 3, pp. 253-259; Jan. 2001 (7 pages).

Coskenseven E. et al., "Comparative Study of Corneal Collagen Cross-linking With Riboflaving and UVA Irradiation in Patients With Keratoconus," *Journal of Refractive Surgery*, vol. 25, issue 4, pp. 371-376; Apr. 2009 (6 pages).

"Definity (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011 (15 pages).

Ehlers W., et al., "Factors Affecting Therapeutic Concentration of Topical Aminocaproic Acid in Traumatic Hyphema," *Investigative Ophthalmology & Visual Science*, vol. 31, No. 11, pp. 2389-2394; Nov. 1990 (6 pages).

Erskine H., "Avedro Becomes Sponsor of US FDA Clinical Trials of Corneal Collagen Crosslinking," Press Release, Mar. 16, 2010 (1 page).

Glenn J.V., et al., "Advanced Glycation End Product (AGE) Accumulation on Bruch's Membrane: Links to Age-Related RPE Dysfunction;" *Investigative Ophthalmology & Visual Science*, vol. 50, No. 1, pp. 441-451; Jan. 2009 (11 pages).

Gravitz L., "Laser Show in the Surgical Suite: Lasers and a century-old dye could supplant needles and thread;" *technology review*, MIT, Mar./Apr. 2009; retrieved from http://www.technologyreview.com/biomedicine/22088/?nlid=1767, on Sep. 26, 2011 (2 pages).

Hafezi F., et al., "Collagen Crosslinking with Ultraviolet-A and Hypoosmolar Riboflavin Solution in Thin Corneas," *J. Catract Refract. Surg.*, vol. 35, No. 1, pp. 621-624; Apr. 2009 (4 pages).

(56) References Cited

OTHER PUBLICATIONS

How to Use Definity: "Frequently Asked Questions;" retrieved from http://www.definityimaging.com/how-faq.html, on Sep. 26, 2011 (3 pages) (date unknown, prior to Apr. 26, 2010).
IMEX, "KXL System: Crosslinking Para Cirugia Corneal Bibliografia Cientifica," Product Literature, Nov. 23, 2010 (24 pages).
Kampik D. et al., "Influence of Corneal Collagen Crosslinking With Riboflavin and Ultraviolet-A Irradiation on Excimer Laser Surgery," *Investigative Opthalmology & Visual Science*, vol. 51, No. 8, pp. 3929-3934; Aug. 2010 (6 pages).
Kissner Anja, et al., "Pharmacological Modification of the Epithelial Permeability by Benzalkonium Chloride in UVA/Riboflavin Corneal Collagen Cross-Linking," *Current Eye Research* 35(8), pp. 715-721; Mar. 2010 (7 pages).
Koller T., et al., "Therapeutische Quervernetzung der Hornhaut mittels UVA and Riboflavin: Therapeutic Cross-Linking of the Cornea Using Riboflavin/UVA," *Klinische Monatsblätter für Augenheilkunde*, vol. 224, No. 9, pp. 700-706; Sep. 2007 (7 pages).
Krueger, Ronald R., "Rapid VS Standard Collagen CXL with Equivalent Energy Dosing," presentation slides, (26 pages); available at http://www.slideshare.net/logen/krueger-herekar-rapid-cross-linking (date unknown, prior to Nov. 9, 2009).
Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).
Muller L., et al., "The Specific Architecture of the Anterior Stroma Accounts for Maintenance of Corneal Curvature," *Br. J. Opthalmol.*, vol. 85, pp. 437-443; Apr. 2001 (8 pages).
Mulroy L., et al., "Photochemical Keratodesmos for repair of Lamellar corneal Incisions;" *Investigative Ophthalmology & Visual Science*, vol. 41, No. 11, pp. 3335-3340; Oct. 2000 (6 pages).
Naoumidi T., et al., "Two-Year Follow-up of Conductive Keratoplasty for the Treatment of Hyperopic Astigmatism," *J. Cataract Refract. Surg.*, vol. 32(5), pp. 732-741; May 2006 (10 pages).
O'Neil A.C., et al., "Microvascular Anastomosis Using a Photochemical Tissue Bonding Technique;" *Lasers in Surgery and Medicine*, vol. 39, Issue 9, pp. 716-722; Oct. 2007 (7 pages).
Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).
Pallikaris I., et al., "Long-term Results of Conductive Keratoplasty for low to Moderate Hyperopia," *J. Cataract Refract. Surg.*, vol. 31(8), pp. 1520-1529; Aug. 2005 (10 pages).
Pinelli R., et al., "C3-Riboflaving Treatments: Where Did We Come From? Where Are We Now?" *Cataract & Refractive Surgery Today Europe*, Summer 2007, pp. 36-46; Jun. 2007 (10 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," *J. Cataract Refract. Surgery*, vol. 35, No. 6, pp. 1055-1062; Jun. 2009 (8 pages).
Proano C.E., et al., "Photochemical Keratodesmos for Bonding Corneal Incisions;" *Investigative Ophthalmology & Visual Science*, vol. 45, No. 7, pp. 2177-2181; Jul. 2004 (5 pages).
Rocha K., et al., "Comparative Study of Riboflavin-UVA Cross-linking and "Flash-linking" Using Surface Wave Elastometry," *Journal of Refractive Surgery*, vol. 24 Issue 7, pp. S748-S751; Sep. 2008 (4 pages).
RxList: "Definity Drug Description;" *The Internet Drug Index*, revised Jun. 16, 2008, retrieved from http://www.rxlist.com/definity-drug.htm, on Sep. 26, 2011 (4 pages).
Sheehan M., et al., "Illumination System for Corneal Collagen Crosslinking," *Optometry and Vision Science*, vol. 88, No. 4, pp. 512-524; Apr. 2011 (13 pages).
Shell, J., "Pharmacokinetics of Topically Applied Ophthalmic Drugs," *Survey of Ophthalmology*, vol. 26, No. 4, pp. 207-218; Jan.-Feb. 1982 (12 pages).

Sonoda S., "Gene Transfer to Corneal Epithelium and Keratocytes Mediated by Ultrasound with Microbubbles," *Investigative Ophthalmology & Visual Science*, vol. 47, No. 2, pp. 558-564; Feb. 2006 (7 pages).
Spoerl E., et al., "Artificial Stiffening of the Cornea by Induction of Intrastromal Cross-links," *Der Ophthalmologe*, vol. 94, No. 12, pp. 902-906; Dec. 1997 (5 pages).
Spoerl E., et al., "Induction of Cross-links in Corneal Tissue," *Experimental Eye Research*, vol. 66, Issue 1, pp. 97-103; Jan. 1998 (7 pages).
Spoerl E., et al., "Techniques for Stiffening the Cornea," *Journal of Refractive Surgery*, vol. 15, Issue 6, pp. 711-713; Nov.-Dec. 1999 (4 pages).
Spoerl E. et al., "Safety of UVA-Riboflavin Cross-Linking of the Cornea," *Cornea*, vol. 26, No. 4, pp. 385-389; May 2007 (5 pages).
Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Trembly et al., "Microwave Thermal Keratoplasty for Myopia: Keratoscopic Evaluation in Porcine Eyes," *Journal of Refractive Surgery*, vol. 17, No. 6, pp. 682-688; Nov./Dec. 2001 (8 pages).
"UV-X: Radiation System for Treatment of Keratokonus," *PESCHKE Meditrade GmbH*; retrieved from http://www.peschkemed.ch/ on Sep. 27, 2011 (1 page) (date unknown, prior to Sep. 16, 2008).
Vasan S., et al., "An agent cleaving glucose-derived protein crosslinks in vitro and in vivo;" *Letters to Nature*, vol. 382, pp. 275-278; Jul. 18, 1996 (4 pages).
Wollensak G., et al., "Collagen Crosslinking of Human and Porcine Sclera," *J. Cataract Refract. Surg.*, vol. 30, Issue 3, pp. 689-695; Mar. 2004 (7 pages).
Wollensak G., et al., "Riboflavin/Ultraviolet-A-induced Collagen Crosslinking for the Treatment of Keratoconus," *American Journal of Ophthalmology*, vol. 135, No. 5, pp. 620-627; May 2003 (8 pages).
Wollensak G., et al., "Cross-linking of Scleral Collagen in the Rabbit Using Riboflavin and UVA," *Acta Ophtalmologica Scandinavica*, vol. 83(4), pp. 477-482; Aug. 2005 (6 pages).
Wollensak G., "Crosslinking Treatment of Progressive Keratoconus: New Hope," *Current Opinion in Ophthalmology*, vol. 17(4), pp. 356-360; Aug. 2006 (5 pages).
Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).
Wollensak G., et al., "Biomechanical and Histological Changes After Corneal Crosslinking With and Without Epithelial Debridement," *J. Cataract Refract. Surg.*, vol. 35, Issue 3, pp. 540-546; Mar. 2009 (7 pages).
Yang H., et al., "3-D Histomorphometry of the Normal and Early Glaucomatous Monkey Optic Nerve Head: Lamina Cribrosa and Peripapillary Scleral Position and Thickness," *Investigative Ophthalmology & Visual Science*, vol. 48, No. 10, pp. 4597-4607; Oct. 2007 (11 pages).
Zderic V., et al., "Drug Delivery Into the Eye With the Use of Ultrasound," *J. Ultrasound Med*, vol. 23(10), pp. 1349-1359; Oct. 2004 (11 pages).
Zderic V., et al., "Ultrasound-enhanced Transcorneal Drug Delivery," *Cornea* vol. 23, No. 8, pp. 804-811; Nov. 2004 (8 pages).
Zang, Y. et al., "Effects of Ultraviolet—A and Riboflavin on the Interaction of Collagen and Proteoglycans during Corneal Cross-linking", Journal of Biological Chemistry, vol. 286, No. 15, dated Apr. 15, 2011 (pp. 13011-13022).
Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969 (7 pages).
Brüel, A., "Changes in Biomechanical Properties, Composition of Collagen and Elastin, and Advanced Glycation Endproducts of the Rat Aorta in Relation to Age," Atherosclerosis 127, Mar. 14, 1996 (11 pages).

(56) References Cited

OTHER PUBLICATIONS

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).
Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).
Frucht-Pery, et al. "Iontophoresis—gentamicin delivery into the rabbit cornea, using a hydrogel delivery probe, " Jun. 20, 2003 (5 pages).
Gibson, Q. et al., "The Oxidation of Reduced Flavin Mononucleotide by Molecular Oxygen," Biochem. J. (1962) 83, 368-377 (10 pages).
Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).
Hitzenberger et al., "Birefringence Properties of the Human Cornea Measured With Polarization Sensitive Optical Coherence Tomography," Bull. Soc. Beige Ophtalmol., 302, 153-168, 2006 (16 pages).
Holmström, B. et al., "Riboflavin As an Electron Donor in Photochemical Reactions," 1867-1871, Nov. 29, 1960 (5 pages).
Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).
Massey, V., "Activation of Molecular Oxygen by Flavins and Flavoproteins," The Journal of Biological Chemistry vol. 269, No. 36, Issue of Sep. 9, pp. 22459-22462, 1994 (4 pages).
Nesterov, A. P. "Transpalpebralny Tonometr Dlya Izmereniya Vnutriglaznogo Davleniya." Feb. 2, 2006. [online] [Retrieved Dec. 17, 2012] Retrieved from the Internet: <URL: http://grpz.ru/images/publication_pdf/27.pdf>.
Rolandi et al. Correlation of Collagen-Linked Fluorescence and Tendon Fiber Breaking Time. Gerontology 1991;27:240-243 (4 pages).
Song P., Metzler D. Photochemical Degradation of Flavins—IV. Studies of the Anaerobic Photolysis of Riboflavin. Photochemistry and Photobiology, vol. 6, pp. 691-709, 1967 (21 pages).
Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).
Yang N., Oster G. Dye-sensitized photopolymerization in the presence of reversible oxygen carriers. J. Phys. Chem. 74, 856-860 (1970) (5 pages).
International Search Report and Written Opinion mailed Oct. 29, 2012 which issued in corresponding International Patent Application No. PCT/US2012/039391 (11 pages).
Averianova, O. S., "Nastoyaschee I buduschee kross-linkage." Mir Ofalmologii, 2010, [online] [retrieved on Feb. 13, 2014] Retrieved from the internet: http://miroft.org.ua/publications/.html (3 pages).
Koller, T. et. Al., "Complication and failure rates after corneal crosslinking, *Journal Cataract and refractive surgery*," vol. 35, No. 8, Aug. 2009, pp. 1358-1362.
Marzouky, et. al., Tensioactive-mediated Transepithelial Corneal Cross-linking—First Laboratory Report, European Ophthalmic Review, 2009, 3(2), pp. 67-70.
O.V. Shilenskaya et al., "Vtorichnaya katarakta posle implantatsii myagkikh IOL," [online] Aug. 21, 2008[retrieved Mar. 4, 2013] Retrieved from the Internet: <URL:http://www.reper.ru/rus/index.php?catid=210> (4 pages).
Thorton, I. et. al., "Biomechancial Effects of Intraocular Pressure Elevation on Optic Berve/Lamina Cribrosa before and after Peripapillary Scleral Collagen Cross-Linking." Invest. Ophthalm,ol. Vis. Sci., Mar. 2009, 50(3): pp. 1227-1233.
Zhang, Y. et al., "Effect of the Synthetic NC-1059 Peptide on Diffusion of Riboflavin Across an Intact Corneal Epithelium", May 6, 2012, ARBO 2012 Annual Meeting Abstract, 140 Stroma and Keratocytes, program number: 1073, poster board number: A109 (1 page).

Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pp. 17-26).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al. "Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Pinelli, R. "Corneal Cross-Linking with Riboflavin: Entering a New Era in Ophthalmology." Ophthalmology Times Europe. vol. 2, No. 7, Sep. 1, 2006 (3 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).
Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).
Barbarino, S. et al., "Post-Lasik ectasia: Stabilization and Effective Management with Riboflavin / ultraviolet A-induced collagen cross-linking," Association for Research in Vision and Ophthalmology, 2006 (1 page).
Burke, JM et al., Abstract for "Retinal proliferation in response to vitreous hemoglobin or iron", Investigative Ophthalmology & Visual Science, May 1981, 20(5), pp. 582-592 (1 page).
Chace, KV. et al., Abstract for "The role of nonenzymatic glycosylation, transition metals, and free radicals in the formation of collagen aggregates", Arch Biochem Biophys., Aug. 1, 1991, 288(2), pp. 473-480 (1 page).
Friedman, M. et al. "Advanced Corneal Cross-Linking System with Fluorescence Dosimetry", Journal of Ophthalmology, vol. 2012, Article ID 303459, dated May 7, 2012 (6 pages).
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UVA-induced collagen cross-linking followed by a limited topo-guided surface excimer ablation," American Academy of Ophthalmology, 2006 (25 pages).
Kanellopoulos, A. J., " Ultraviolet A cornea collagen cross-linking, as a pre-treatment for surface excimer ablation in the management of keratoconus and post-LASIK ectasia," American Academy of Ophthalmology, 2005 (28 pages).
Meek, K.M. et al. "The Cornea and Scleera", Collagen: Structure and Mechanics, Chapter 13, pp. 359-396, 2008 (38 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Pinelli R., "Resultados de la Sociedad de Cirugia Refractiva Italiana (SICR) utilizando el C3-R" presented at the Istitutor Laser Microchirurgia Oculare in 2007 in Italy (23 pages).
Pinelli R., "The Italian Refractive Surgery Society (SICR) results using C3-R" presented Jun. 22-23, 2007 in Italy (13 pages).
Randall, J. et al., "The Measurementand Intrepretation of Brillouin Scattering in the Lens of the Eye," The Royal Society, Abstract only, published 2013 [available online at http://rspb.royalsocietypublishing.org/214/1197/449.short] (1 page).
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).

(56) References Cited

OTHER PUBLICATIONS

Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).

Scarcelli, G. et al., "Brillouin Optical Microscopy for Corneal Biomechanics", Investigative Ophthalmology & Visual Science, Jan. 2012, vol. 53, No. 1, pp. 185-190 (6 pages).

Sun, G.J. et al., Abstract for "Properties of 2,3-butanedione and 1-phenyl-1,2-propanedione as new photosensitizers for visible light cured dental resin composites", Polymer 41, pp. 6205-6212, published in 2000 (1 page).

Tomlinson, A. "Tear Film Osmolarity: Determination of a Referent for Dry Eye Diagnosis", Investigative Ophthalmology & Visual Science, Oct. 2006, vol. 47, No. 10, pp. 4309-4315 (7 page).

Turgunbaev N.A. et al. Fotomodifikatsiya sklery u bolnykh s progressiruyuschei blizorukostyu (predvaritelnoe soobschenie). 2010 [online] Retrieved from the Internet:<URL: http://www.eyepress.ru/article.aspx?7484> (2 pages).

Wong, J. et al., "Post-Lasik ectasia: PRK following previous stablization and effective management with Riboflavin / ultraviolet A-induced collagen cross-linking," Association for Research in Vision and Ophthalmology, 2006 (1 page).

International Search Report and Written Opinion for PCT/US2013/068588, mailed Feb. 6, 2014 (6 pages).

* cited by examiner

SYSTEMS AND METHODS FOR RESHAPING AN EYE FEATURE

CROSS REFERENCE TO RELATED APPLICATIONS

This Application claims the benefit of, and priority to, U.S. Provisional Patent Application No. 61/489,554, filed May 24, 2011, and U.S. Provisional Patent Application No. 61/492,499, filed Jun. 2, 2011, the contents of these applications being incorporated entirely herein by reference.

FIELD OF THE INVENTION

The present invention relates generally to systems and methods for conducting an eye treatment. In particular, the present invention relates to systems and methods for achieving corrective changes in corneal tissue and improving the stability of the changes to the corneal tissue.

BACKGROUND

A variety of eye disorders, such as myopia, keratoconus, and hyperopia, involve abnormal shaping of the cornea. Laser-assisted in-situ keratomileusis (LASIK) is one of a number of corrective procedures that reshape the cornea so that light traveling through the cornea is properly focused onto the retina located in the back of the eye. During LASIK surgery, an instrument called a microkeratome is used to cut a thin flap in the cornea. The corneal flap is then peeled back and the underlying corneal tissue is ablated to the desired shape with an excimer laser. After the desired reshaping of the cornea is achieved, the corneal flap is put back in place and the surgery is complete.

In another corrective procedure that reshapes the cornea, thermokeratoplasty provides a noninvasive procedure that applies electrical energy in the microwave or radio frequency (RF) band to the cornea. In particular, the electrical energy raises the corneal temperature until the collagen fibers in the cornea shrink at about 60° C. The onset of shrinkage is rapid, and stresses resulting from this shrinkage reshape the corneal surface. Thus, application of energy according to particular patterns, including, but not limited to, circular or annular patterns, causes aspects of the cornea to flatten and improves vision in the eye.

BRIEF SUMMARY

Embodiments according to aspects of the present invention provide systems and methods for achieving corrective changes in corneal tissue and improving the stability of the changes to the corneal tissue.

In some embodiments, a system for treating an eye includes a cutting instrument that creates incisions in selected areas of the cornea. The system also includes an eye therapy system that applies reshaping forces to the cornea. The system further includes a controller that determines the selected areas of the cornea for the incisions and the reshaping forces from the eye therapy system, such that the reshaping forces and the incisions combine to achieve a predetermined corrective reshaping of the cornea.

Correspondingly, a method for treating an eye includes creating, with a cutting instrument, incisions in selected areas of the cornea. The method also includes applying, with an eye therapy system, reshaping forces to the cornea. The method further includes determining the selected areas of the cornea for the incisions and the reshaping forces from the eye therapy system, such that the reshaping forces and the incisions combine to achieve a predetermined corrective reshaping of the cornea.

In examples of the embodiments above, the cutting instrument includes a femtosecond laser. In other examples, the eye therapy system includes a LASIK surgery system or a thermokeratoplasty system. In yet other examples, the eye therapy system includes a cross-linking treatment system, where the cross-linking treatment system includes an applicator that applies a cross-linking agent to the cornea, a light source that provides photoactivating light for the cross-linking agent, and optical elements that direct the photoactivating light to selected areas of the cornea with the applied cross-linking agent, the photoactivating light acting on the cross-linking agent initiating cross-linking activity in the selected areas to apply the reshaping forces. In further examples, the cross-linking agent includes Riboflavin and the photoactivating light is ultraviolet light. In additional examples, the cutting instrument creates incisions in posterior corneal tissue.

In other embodiments, a method for treating an eye includes measuring an eye to determine a required amount of reshaping of a cornea of the eye. The method also includes determining one or more doses of cross-linking agent and one or more corresponding doses of photoactivating light according to the required amount of reshaping of the cornea. The method further includes applying the one or more doses of cross-linking agent to the cornea. Additionally, the method includes delivering, from a light source, the one or more doses of photoactivating light to the area of the eye, the one or more doses of ultraviolet light combining with the one or more doses of cross-linking agent to induce the corrective reshaping of the cornea. The method may further include prior to measuring the eye, applying a treatment to an eye, the treatment requiring the corrective reshaping of the cornea. In one example, the cross-linking agent includes Riboflavin, and the one or more doses of photoactivating light includes a dose of ultraviolet light greater than approximately 5.4 J/cm$^2$.

These and other aspects of the present disclosure will become more apparent from the following detailed description of embodiments of the present disclosure when viewed in conjunction with the accompanying drawings.

Figure 1:
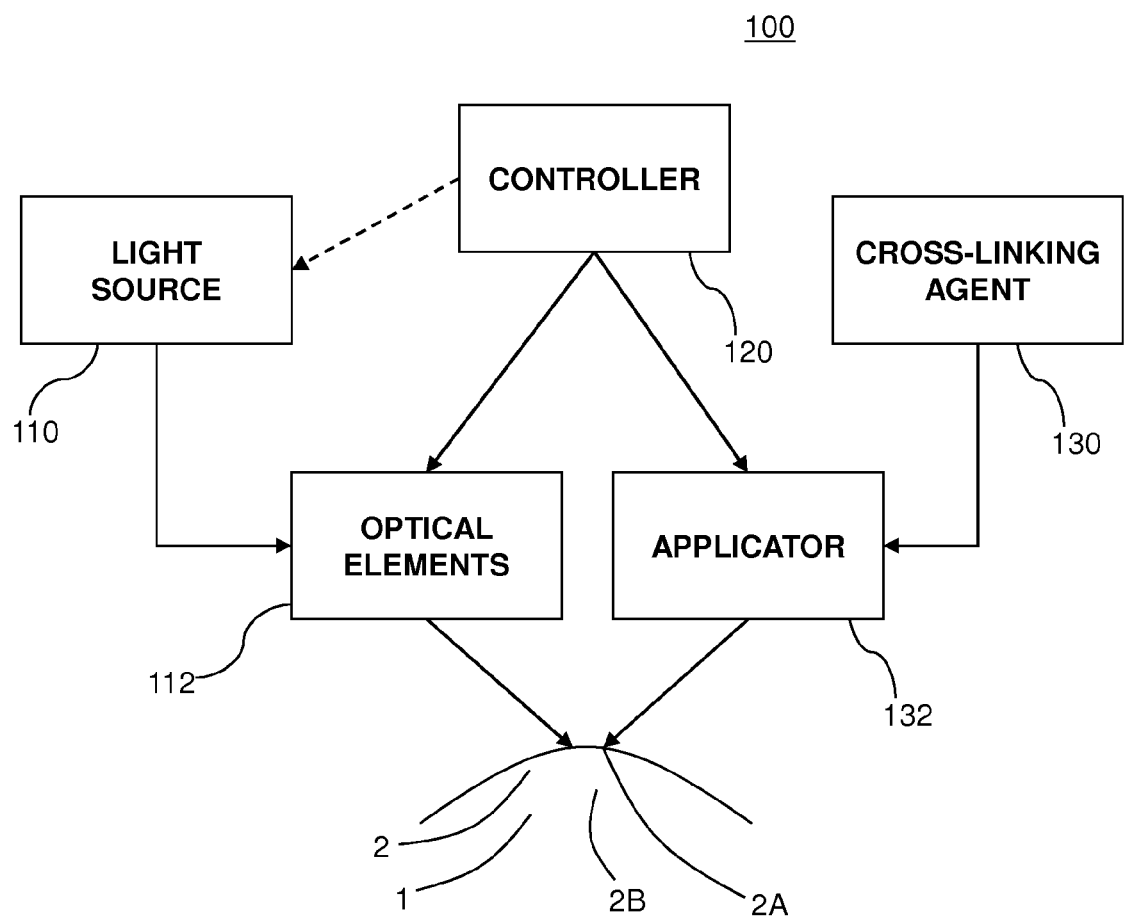
FIG. 1 illustrates an example system for delivering a cross-linking agent and initiating cross-linking.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit of the invention.

DETAILED DESCRIPTION

According to some embodiments, a cross-linking agent is applied to regions of the cornea treated by LASIK surgery, thermokeratoplasty, or other eye treatment. In particular, the cross-linking agent may be applied to initiate molecular cross-linking of corneal collagen to stabilize corneal tissue and improve its biomechanical strength when an eye treatment is employed to make corrections to corneal structure and shape.

FIG. 1 provides a block diagram of an example delivery system 100 for delivering a cross-linking agent 130 and an initiating element, e.g., light, to a cornea 2 of an eye 1 in order to initiate molecular cross-linking of corneal collagen within the cornea 2. Cross-linking can stabilize corneal tissue and improve its biomechanical strength. The delivery system 100 includes an applicator 132 for applying the cross-linking agent 130 to the cornea 2. The delivery system 100 includes a light source 110 and optical elements 112 for directing light to the cornea 2. The delivery system 100 also includes a controller 120 that is coupled to the applicator 132 and the optical elements 112. The applicator 132 may be an apparatus adapted to apply the cross-linking agent 130 according to particular patterns on the cornea 2 where cross-linking activity may be more advantageous.

The optical elements 112 may include, for example, one or more mirrors or lenses for directing and focusing the light emitted by the light source 110 to a particular pattern on the cornea 2 suitable for activating the cross-linking agent 130. The light source 110 may be an ultraviolet (UV) light source, and the light directed to the cornea 2 through the optical elements 112 activates the cross-linking agent 130. The light source 110 may also alternatively or additionally emit photons with greater or lesser energy levels than UV light photons. The delivery system 100 also includes a controller 120 for controlling the operation of the optical elements 112 or the applicator 132, or both. By controlling aspects of the operation of the optical elements 112 and the applicator 132, the controller 120 can control the regions of the cornea 2 that receive the cross-linking agent 130 and that are exposed to the light source 110. By controlling the regions of the cornea 2 that receive the cross-linking agent 130 and the light source 110, the controller 120 can control the particular regions of the cornea 2 that are strengthened and stabilized through cross-linking of the corneal collagen fibrils. In an implementation, the cross-linking agent 130 can be applied generally to the eye 1, without regard to a particular region of the cornea 2 requiring strengthening, but the light source 110 can be selectively directed to particular regions of the cornea 2 requiring strengthening, and thereby control the region of the cornea 2 wherein cross-linking is initiated by controlling the regions of the cornea 2 that are exposed to the light source 110.

The optical elements 112 can be used to focus the light emitted by the light source 110 to a particular focal plane within the cornea 2, such as a focal plane that includes the mid-depth region 2B. In addition, according to particular embodiments, the optical elements 112 may include one or more beam splitters for dividing a beam of light emitted by the light source 110, and may include one or more heat sinks for absorbing light emitted by the light source 110. The optical elements 112 may further include filters for partially blocking wavelengths of light emitted by the light source 110 and for advantageously selecting particular wavelengths of light to be directed to the cornea 2 for activating the cross-linking agent 130. The controller 120 can also be adapted to control the light source 110 by, for example, toggling a power switch of the light source 110.

In an implementation, the controller 120 may include hardware and/or software elements, and may be a computer. The controller 120 may include a processor, a memory storage, a microcontroller, digital logic elements, software running on a computer processor, or any combination thereof. In an alternative implementation of the delivery system 100 shown in FIG. 1, the controller 120 may be replaced by two or more separate controllers or processors. For example, one controller may be used to control the operation of the applicator 132, and thereby control the precise rate and location of the application of the cross-linking agent 130 to the cornea 2. Another controller may be used to control the operation of the optical elements 112, and thereby control with precision the delivery of the light from the light source 110 to the cornea 2 by controlling any combination of: wavelength, bandwidth, intensity, power, location, depth of penetration, and duration of treatment. In addition, the function of the controller 120 can be partially or wholly replaced by a manual operation. For example, the applicator 132 can be manually operated to deliver the cross-linking agent 130 to the cornea 2 without the assistance of the controller 120. In addition, the controller 120 can operate the applicator 132 and the optical elements 112 according to inputs dynamically supplied by an operator of the delivery system 100 in real time, or can operate according to a pre-programmed sequence or routine.

Aspects of devices and approaches for applying a cross-linking agent to the cornea and delivering light to activate the applied cross-linking agent are described in U.S. application Ser. No. 13/051,699, filed Mar. 18, 2011, and U.S. application Ser. No. 13/438,705, filed Apr. 12, 2012, the contents of these applications being incorporated entirely herein by reference.

Figure 2A:
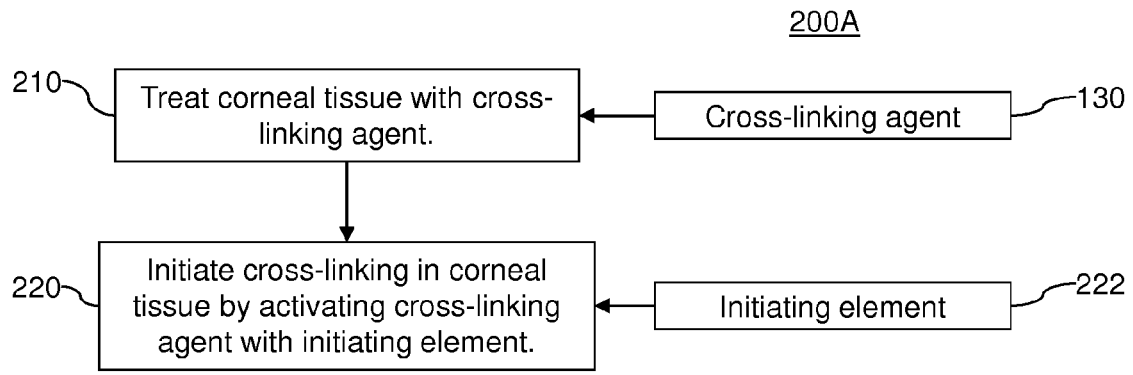
FIG. 2A illustrates an example cross-linking treatment.
Figure 2B:
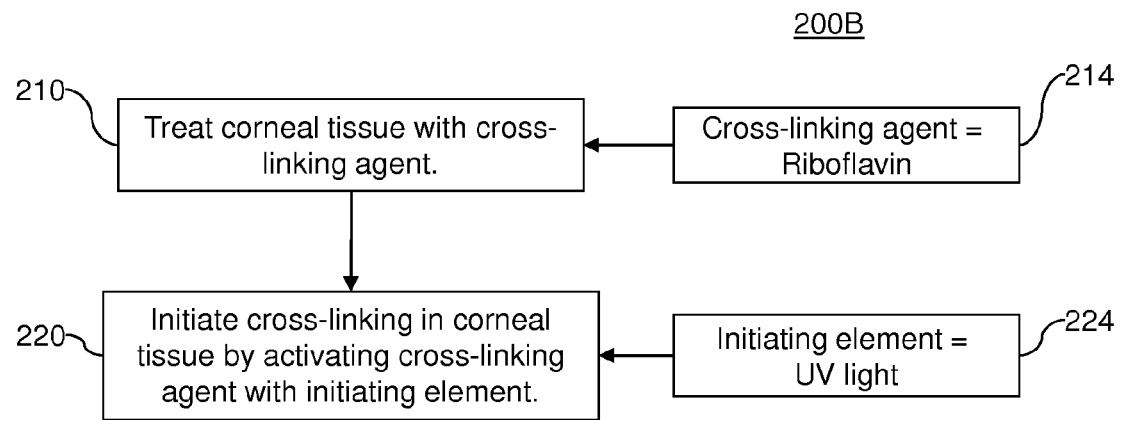
FIG. 2B illustrates an example cross-linking treatment, where the cross-linking agent is Riboflavin and the initiating element is ultraviolet (UV) light.

FIGS. 2A-2B describe an exemplary operation of the delivery system 100, where the cross-linking agent 130 is applied to the cornea 2 using the applicator 132. Once the cross-linking agent 130 has been applied to the cornea 2, the cross-linking agent 130 is initiated by light from the light source 110 to cause cross-linking agent 130 to absorb enough energy to release cross-linking agent radicals and free oxygen radicals within the cornea 2. Once released, the cross-linking agent radicals and free oxygen radicals (i.e. singlet oxygen) form covalent bonds between corneal collagen fibrils and thereby cause the corneal collagen fibrils to cross-link and change the structure of the cornea 2. For example, activation of the cross-linking agent 130 with the light source 110 delivered to the cornea 2 through the optical elements 112 may result in cross-linking in the mid-depth region 2B of the cornea 2 and thereby strengthen and stiffen the structure of the cornea 2.

Referring to FIG. 2A, an example embodiment 200A is illustrated. Specifically, in step 210, the corneal tissue is treated with the cross-linking agent 130. Step 210 may occur, for example, after a treatment is applied to generate structural changes in the cornea and produce a desired shape change. Alternatively, step 210 may occur, for example, after it has been determined that the corneal tissue requires stabilization or strengthening. The cross-linking agent 130 is then activated in step 220 with an initiating element 222. Activation of the cross-linking agent 130, for example, may be triggered thermally by the application of microwaves or light. In an example configuration, the initiating element 222 may be the light from the light source 110 shown in FIG. 1.

As the example embodiment 200B of FIG. 2B shows further, Riboflavin may be applied topically as a cross-linking agent 214 to the corneal tissue in step 210. As also shown in FIG. 2B, UV light may be applied as an initiating element 224 in step 220 to initiate cross-linking in the corneal areas treated with Riboflavin. Specifically, the UV light initiates cross-linking activity by causing the applied Riboflavin to release Riboflavin radicals and reactive oxygen radicals in the corneal tissue. In particular, the Riboflavin acts as a sensitizer to create Riboflavin radicals and to convert $O_2$ into singlet oxygen which causes cross-linking within the corneal tissue.

The cross-linking agent 130 may be applied to the corneal tissue in an ophthalmic solution, e.g., from an eye dropper, syringe, or the like. In some cases, the cross-linking agent 130 is effectively applied to the corneal tissue after removal of the overlying epithelium. However, in other cases, the cross-linking agent 130 is effectively applied in a solution that transitions across the epithelium into the underlying corneal tissue, i.e., without removal of the epithelium. For example, a transepithelial solution may combine Riboflavin with approximately 0.1% benzalkonium chloride (BAC) in distilled water. Alternatively, the transepithelial solution may include other salt mixtures, such as a solution containing approximately 0.4% sodium chloride (NaCl) and approximately 0.02% BAC. Additionally, the transepithelial solution may contain methyl cellulose, dextran, or the like to provide a desired viscosity that allows the solution to remain on the eye for a determined soak time.

Although treatments, such as LASIK surgery or thermokeratoplasty, may initially achieve desired reshaping of the cornea 2, the desired effects of reshaping the cornea 2 may be mitigated or reversed at least partially if the collagen fibrils within the cornea 2 continue to change after the desired reshaping has been achieved. Indeed, complications may result from further changes to the cornea 2 after treatment. For example, a complication known as post-LASIK ectasia may occur due to the permanent thinning and weakening of the cornea 2 caused by LASIK surgery. In post-LASIK ectasia, the cornea 2 experiences progressive steepening (bulging).

Therefore, embodiments may preserve the desired corneal structure and shape that result from treatments, such as LASIK surgery or thermokeratoplasty. In particular, such embodiments provide approaches for initiating molecular cross-linking of the corneal collagen to stabilize the corneal tissue and improve its biomechanical strength and stiffness after the desired shape change has been achieved. The system 100 described above may be employed to initiate cross-linking activity in combination with a shape changing treatment. In addition, embodiments may provide devices and approaches for monitoring cross-linking in the corneal collagen and the resulting changes in biomechanical strength to provide a feedback to a system for inducing cross-linking in corneal tissue. Such devices and approaches are described in detail in U.S. application Ser. No. 13/051,699, filed Mar. 18, 2011, and U.S. application Ser. No. 13/438,705, filed Apr. 12, 2012, referenced above.

The amount of time required to achieve the desired cross-linking can be controlled by adjusting the parameters for delivery and activation of the cross-linking agent. In an example implementation, the time can be reduced from minutes to seconds. While some configurations may apply the initiating element (e.g., from the light source 110) at a flux dose of approximately J/cm2, embodiments allow larger doses of the initiating element to be applied to reduce the time required to achieve the desired cross-linking. Conventional Riboflavin treatments apply UV light at a standard dose of approximately 5.4 J/cm2. Larger doses are not applied, for example, due to conventional understandings regarding the safe application of UV light to the cornea. It has been discovered that larger doses of UV light may be safely and effectively applied. For example, the UV light may be applied in a dose of approximately 9 J/cm2. Highly accelerated cross-linking is particularly possible with the devices and approaches described in detail in U.S. application Ser. No. 13/051,699, filed Mar. 18, 2011, and U.S. application Ser. No. 13/438,705, filed Apr. 12, 2012, referenced above.

To decrease the treatment time, and advantageously generate stronger cross-linking within the cornea 2, the initiating element (e.g., the light source 110) may be applied with a power between 30 mW and 1 W. The total dose of energy absorbed in the cornea 2 can be described as an effective dose, which is an amount of energy absorbed through a region of the corneal surface 2A. For example the effective dose for a region of the cornea 2 can be, for example, 5 J/cm2, or as high as 20 J/cm2 or 30 J/cm2. The effective dose delivering the energy flux just described can be delivered from a single application of energy, or from repeated applications of energy. In an example implementation where repeated applications of energy are employed to deliver an effective dose to a region of the cornea 2, each subsequent application of energy can be identical, or can be different according to information provided by a feedback system.

Surprising results and unforeseen effects on corneal structure have been observed with the application of higher doses of UV light. Typical cross-linking activity from applying Riboflavin and UV light at a dose of approximately 5.4 J/cm$^2$ to a stable eye (without keratoconus) does not induce significant flattening of the eye. The cross-linking treatment may yield, for example, approximately 0.5 Diopters of flattening. It has been discovered, however, that when applying higher doses of UV light to a cornea treated with Riboflavin after thermokeratoplasty, the cross-linking activity enhances the shape change from the thermokeratoplasty. For example, in eight patients receiving thermokeratoplasty and cross-linking treatments, the cross-linking activity was able to provide almost 4 Diopters of flattening in addition to the flattening produced by the thermokeratoplasty.

Accordingly, further embodiments may apply Riboflavin and higher doses (i.e., greater than approximately 5.4 J/cm$^2$) of photoactivating light to produce additional shape change, i.e., flattening. In particular, spatially patterned cross-linking activity may be employed to provide non-invasive correction of errors that result from the primary application of treatments, LASIK surgery or thermokertoplasty. Such treatments often require some type of follow-up procedure to correct for any, even minor, refractive error that remains. Thus, in addition to stabilizing shapes changes, Riboflavin may be employed as a post-procedural corrective treatment.

As another example of a post-procedural corrective treatment, cross-linking treatments may be employed after cataract surgery. Cataract surgery involves the removal of the natural lens of the eye that has developed an opacification, i.e., a cataract, and the implantation of an artificial intraocular lens. After cataract surgery, patients may have residual myopia and/or surgically induced astigmatism. Embodiments address these post-procedural errors through subsequent cross-linking treatment. Post-procedural errors, including higher order aberrations, have always been a concern with cataract surgery. Conventionally, post-procedural errors are addressed by additional ablation. The regions upon which ablation techniques may be applied, however, are limited. Advantageously, the post-procedural cross-linking treatment may be applied more easily and non-invasively, e.g., transepithelially.

Figure 3:
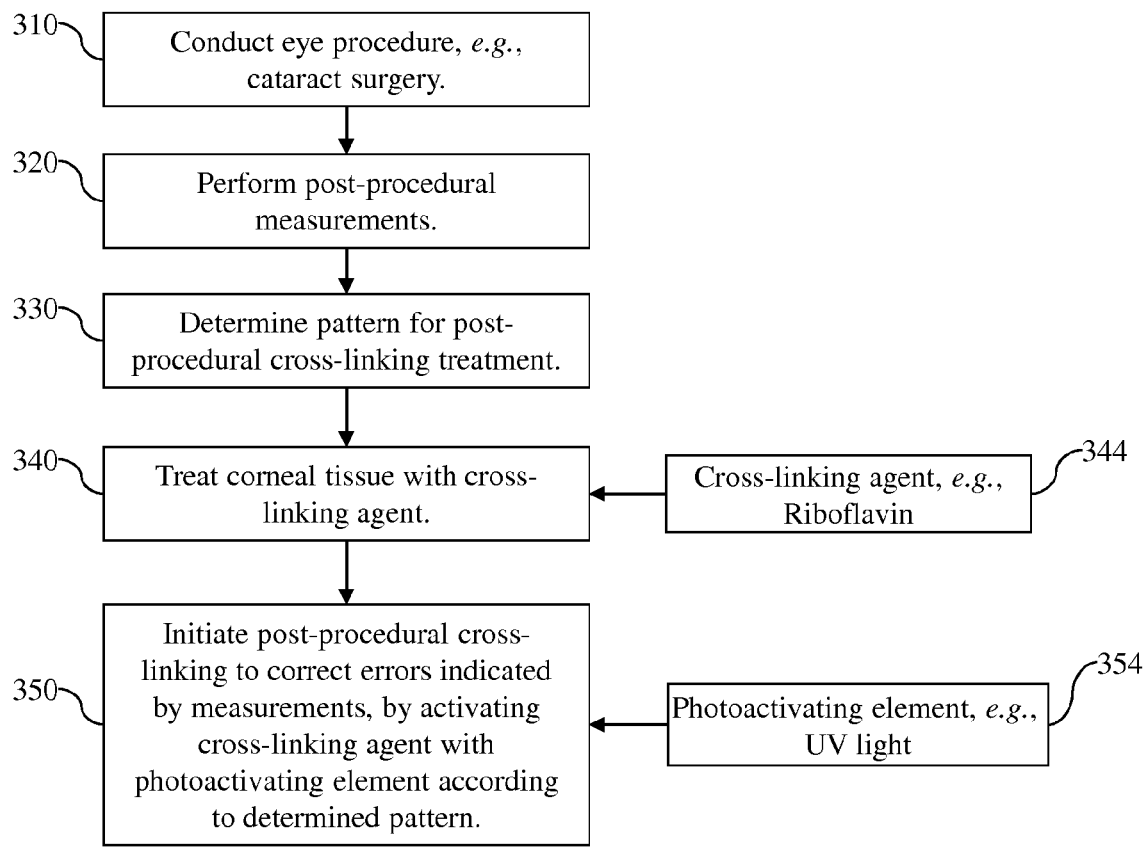
FIG. 3 illustrates an example cross-linking treatment applied after an eye procedure.

Referring to FIG. 3, a procedure, such as cataract surgery, is conducted in step 310. In step 320, a measurement device performs post-procedural measurements to obtain topographic data of the cornea and identify any post-procedural refractive errors, including spherical aberrations of any order. In step 330, a spatial pattern for post-procedural cross-linking treatment is determined from the measurements. In other words, the measurements spatially guide the post-procedural cross-linking treatment. The spatial pattern includes indications for the energy and power applied to the cornea with the photoactivating light. In steps 340 and 350, the post-procedural cross-linking treatment is applied to induce the shape change that addresses and corrects the refractive errors. The cross-linking agent 344 is applied and the photoactivating light 354 is applied in appropriate doses in a beam that follows the spatial pattern determined in step 330. As described above, the post-procedural cross-linking treatment induces the desired corrective shape change.

Thus, according to some embodiments, systems for treating disorders of the eye are configured to measure post-procedural refractive errors and to determine and generate cross-linking activity according to a spatial pattern to address these errors. In particular, such systems may include known measurement devices that measure the topography of the eye. In addition, such systems may include a controller, e.g., a computer processing system that reads instructions on computer-readable storage media, to apply an algorithm to determine the spatial pattern for cross-linking activity. The systems may also include devices for applying the cross-linking agent and applying the photoactivating light according to the spatial pattern. In some embodiments, the controller may also be used to control the application of the photoactivating light. Aspects of systems and approaches for making measurements, applying a cross-linking agent to the cornea, and delivering light to activate the applied cross-linking agent are described in U.S. application Ser. No. 13/051,699, filed Mar. 18, 2011, and U.S. application Ser. No. 13/438,705, filed Apr. 12, 2012, referenced above.

In sum, cross-linking treatments can be applied after corrective procedures (e.g., LASIK surgery, thermokeratoplasty, or cataract surgery) to induce additional reshaping of the cornea. Such applications of a cross-linking agent, however, suggest that cross-linking treatments can be applied more broadly and independently of other corrective procedures to achieve a desired reshaping of the cornea. In other words, cross-linking treatment can be applied on its own as a corrective procedure and is not limited as a post-procedural treatment. Although reshaping of corneal tissue through the independent application of a cross-linking, e.g., Riboflavin, may be achieved with high doses of an initiating element, e.g., a UV dose of greater than approximately 5.4 $J/cm^2$, it is contemplated that at least some corrective reshaping may be achieved with lower doses.

Generally, eye treatments, such as LASIK surgery or thermokeratoplasty, involve procedures to the anterior corneal tissue. While the procedures achieve a direct change in the shape of the anterior corneal tissue, the posterior corneal tissue generally does not change shape in a corresponding fashion. Accordingly, after such procedures, the posterior corneal tissue may exert a force on the anterior corneal tissue that counters or inhibits the desired changes to the corneal tissue affected by the procedures. The forces applied by the posterior corneal tissue on the anterior corneal tissue may prevent the procedure from achieving the desired structural change. As a result, for example, more severe ablation of corneal tissue, greater amounts of thermal energy, and/or greater amounts of cross-linking agents may be required to account for the force applied by the posterior corneal tissue on the anterior corneal tissue and achieve a desired change to the corneal tissue.

Embodiments also relate to systems and processes for conducting an eye treatment that address such problems. In particular, embodiments involve a procedure to cut one or more dissection planes or regions in the cornea to at least partially disassociate or separate the anterior corneal tissue from the posterior corneal tissue to provide one or more areas of stress relief. By providing one or more areas of stress relief, embodiments reduce the extent of eye treatment required to achieve a desired change in corneal tissue and improve the stability of changes to the corneal tissue as part of eye treatment.

Figure 4:
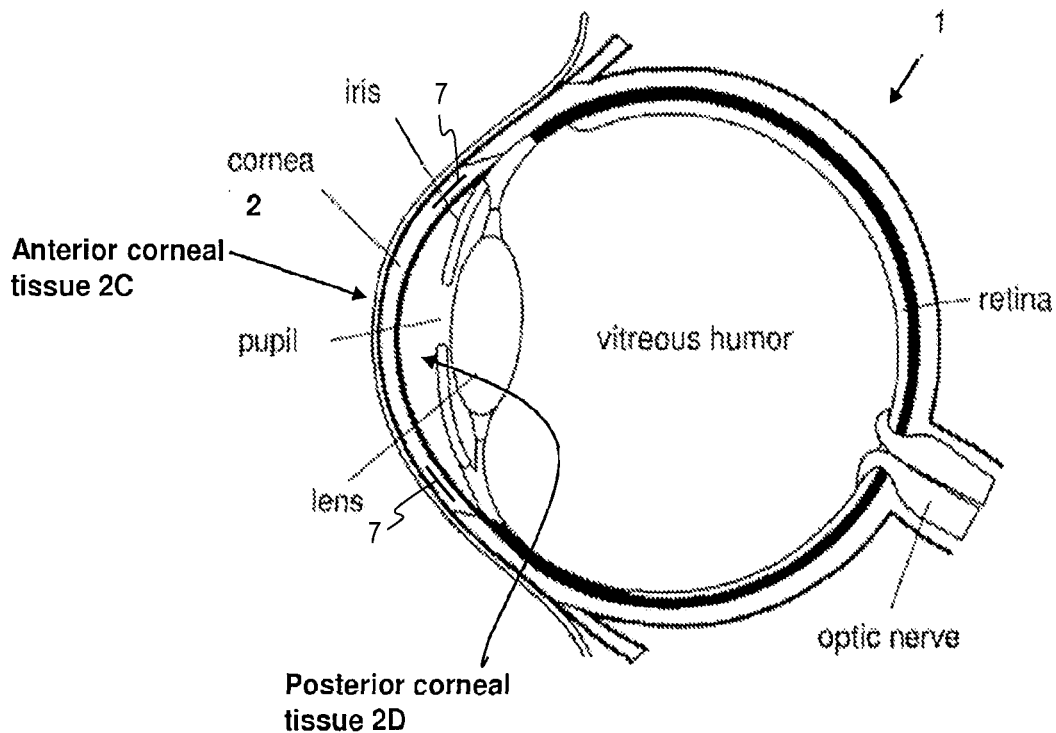
FIG. 4 illustrates aspects of an eye anatomy.
Figure 5:
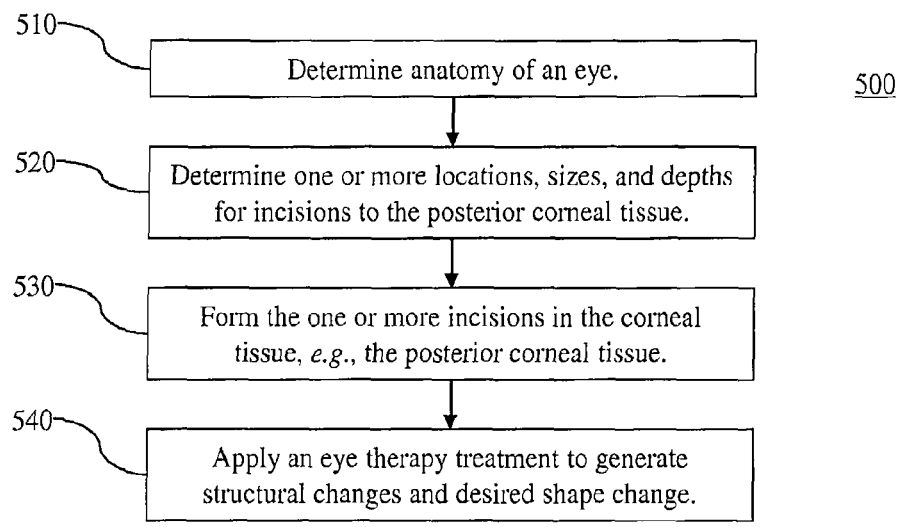
FIG. 5 illustrates an example treatment that makes incisions to corneal tissue prior to an eye treatment that causes shape change in the cornea.

FIG. 4 illustrates a cornea 2 of an eye 1, including an anterior corneal tissue 2C and a posterior corneal tissue 2D. FIG. 5 illustrates an example process 500 for performing a treatment on an eye. In step 510, the anatomy of a patient's eye 1 is determined using a measurement device. The determination of the eye 1 anatomy may include, for example, a determination of the curvature and the thickness of the anterior corneal tissue 2C and the posterior corneal tissue 2D. Non-limiting examples of measurement devices that are suitable to assist in determining the anatomy of the eye 1 include a tonometer, an ultrasound pachymeter, an optical pachymeter, and/or an imaging device. Aspects of systems and approaches for making such measurements are described in U.S. application Ser. No. 13/051,699, filed Mar. 18, 2011, and U.S. application Ser. No. 13/438,705, filed Apr. 12, 2012, referenced above.

At step 520, one or more locations, sizes, and depths are determined for one or more incisions to be formed in the posterior corneal tissue 2C. The locations, sizes, and depths of the one or more incisions to the posterior corneal tissue 2D depend on the anatomical structure of the patient's eye (e.g., cornea 2), the particular optical condition that is to be corrected (e.g., myopia, keratoconus, or hyperopia), and/or the type of eye treatment to be applied (e.g., themokeratoplasty or LASIK) to reshape the cornea 2. In particular, the location, size, and depth of the one or more incisions are determined so as to at least partially disassociate or separate the anterior corneal tissue 2C from the posterior corneal tissue 2D without weakening the structural integrity of the eye 1. Accordingly, the one or more incisions may take the form of one or more dissection planes or regions. The one or more dissection planes or regions can be optimized for particular applications by, for example, localizing the one or more incisions to a specific region or providing the one or more incisions in a particular pattern depending on the anatomical structure of the patient's eye, the optical condition corrected, and/or the method of eye treatment employed.

To avoid a weakening of the structural integrity of the eye 1, the location, size, and depth of the one or more incisions are generally determined so that the incisions do not penetrate through the full thickness of the cornea 2 (i.e., from the posterior corneal tissue 2D through the anterior corneal tissue 2C). In some embodiments, it is contemplated that the one or more incisions may be determined to have a location, size, and depth such that the one or more incisions formed in the posterior corneal tissue 2D do not penetrate into any portion of the anterior corneal tissue 2C. According to some embodiments, the one or more locations, sizes, and depths for the one or more incisions may be determined and/or optimized by a controller (e.g., a computer processing system that reads instructions on computer-readable storage media).

At step 530, the one or more incisions are formed in the posterior corneal tissue 2 by an incision device according to the one or more locations, sizes, and depths determined at step 520. As a non-limiting example, the incision device can be a femtosecond pulsed laser that is configured or controlled (e.g., by one or more controllers) to form the desired one or more incisions. The one or more incisions at least partially disassociate or separate the posterior corneal tissue 2D from the anterior corneal tissue 2C so as to provide for one or more areas of stress relief.

An eye treatment (e.g., LASIK surgery, themokeratoplasty, or cross-linking treatment) is applied at step 540 to generate structural changes in the anterior corneal tissue 2C and produce a desired shape change. The system for applying the eye treatment may include any device that is suitable for applying, for example, LASIK surgery or thermokeratoplasty. One non-limiting example of a device for applying LASIK is an excimer laser. A non-limiting example of an applicator for thermokeratoplasty is described in U.S. patent application Ser. No. 12/208,963, filed Sep. 11, 2008, which is a continuation-in-part of U.S. patent application Ser. No. 11/898,189, filed Sep. 10, 2007, the contents of these applications being entirely incorporated herein by reference.

Advantageously, the eye treatment applied to the eye 1 may take into account the reduced forces that the posterior corneal tissue 2D exerts on the anterior corneal tissue 2C due to the one or more incisions. As a result, the extent of eye treatment required to achieve a desired change in corneal tissue may be reduced. For example, in a LASIK eye treatment procedure, a more moderate ablation of anterior corneal tissue 2C may be required to achieve a desired change in the corneal shape. Similarly, for example, with thermokeratoplasty, a lower magnitude of electrical energy, a smaller electrical energy pattern, or a reduced number of electrical energy pulses may be required to achieve a desired change in the corneal shape. Likewise, in a cross-linking treatment, a reduced amount of cross-linking agent or lower dose of UV light may be required to achieve a desired reshaping of the corneal shape. Accordingly, the precise amount of treatment to be applied to the eye (e.g., laser ablation, magnitude of electrical energy, size of electrical energy pattern, number of electrical pulses, amount of cross-linking agent, and/or dose of UV light) can be determined and controlled by one or more controllers that take into account the anatomy of the patient's eye and the one or more incisions to the posterior corneal tissue 2D.

Additionally, after the application of the eye treatment at step 540, the resulting shape of the anterior corneal tissue 2C may exhibit greater stability as the one or more incisions provide area(s) of stress relief against the forces applied by the posterior corneal tissue 2D to the anterior corneal tissue 2C. Optionally, at step 550, a cross-linking agent can be further applied to the cornea 2 to stabilize the corneal tissue 2 and improve its biomechanical strength, e.g., in combination with LASIK surgery or thermokeratoplasty, as described above.

The embodiment described with reference to FIG. 5 provides an example in which incisions are employed to promote desired shape change in corneal structure. Indeed, it is contemplated that such incisions are not limited to posterior corneal tissue. In general, a cutting instrument, such as a femtosecond laser, may be employed to make incisions in any portion of the cornea to create slip planes 7 that allow aspects of the corneal structure to move more easily relative to each other and to allow desired reshaping to take place when combined with other eye treatments, such as LASIK surgery, thermokeratoplasty, or cross-linking treatment. Indeed, it is contemplated that some particular shape changes would not be otherwise possible without the creation of one or more slip planes 7. The location, size, depth of the slip planes 7 depends on the desired shape change.

Figure 6:
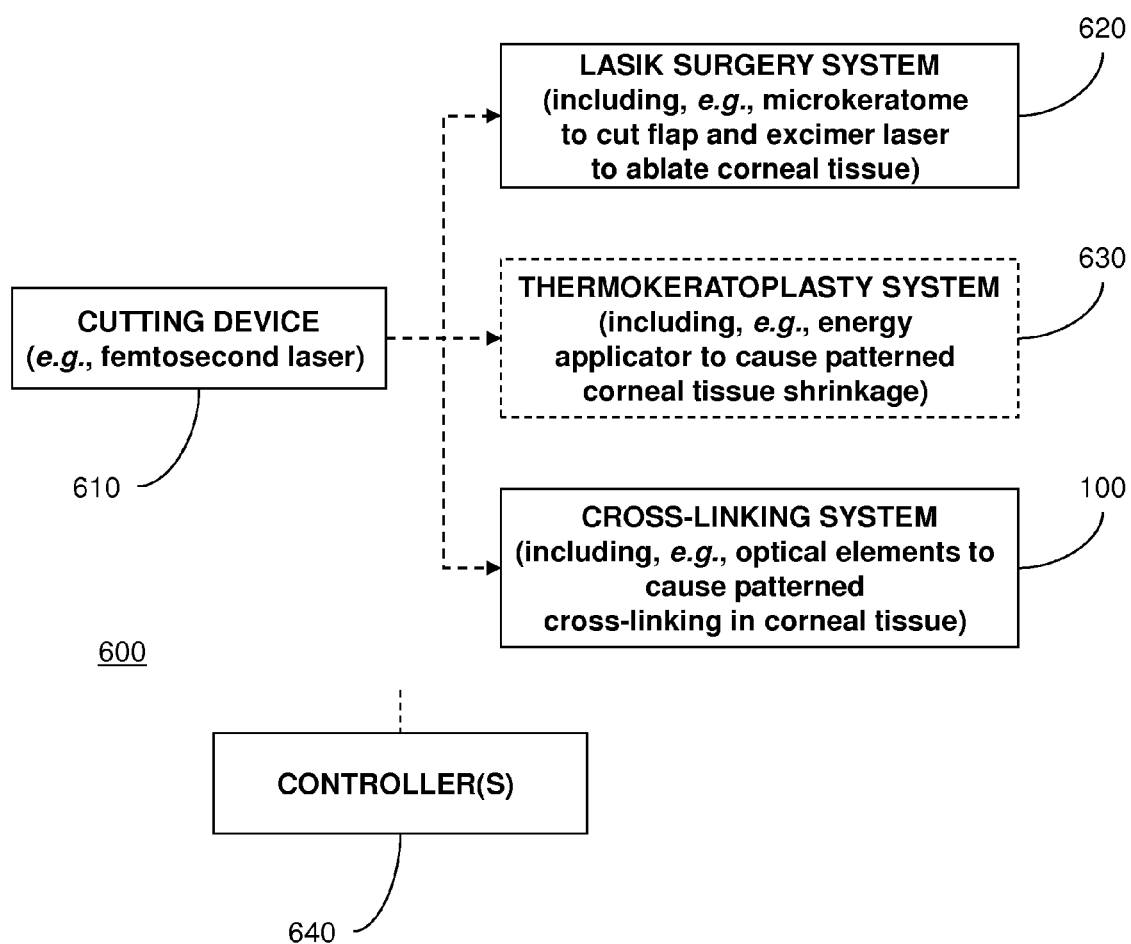
FIG. 6 illustrates an example system that makes incisions to corneal tissue prior to an eye treatment that causes shape change in the cornea.

FIG. 6 illustrates an example integrated system 600, in which the components can be employed to manipulate varying aspects of the corneal structure in order to achieve customized shape change. In particular, a cutting instrument 610, e.g., femtosecond laser, is combined with at least one eye treatment system: a LASIK surgery system 620, a thermokeratoplasty system 630, and/or the cross-linking system 100 as described with reference to FIG. 1. The components of the system 600 can be controlled by one or more controllers 640, which make measurements, provide monitoring, and/or drive the components, e.g., based on feedback from the monitoring.

Thus, in operation, the cutting instrument is employed to create incisions in selected areas of the cornea. One of the eye therapy systems applies reshaping forces to the cornea. For example, the LASIK surgery system 620 ablates the corneal tissue with an excimer laser to apply the reshaping forces after a microkeratome creates a corneal flap; the thermokeratoplasty system 630 applies energy, with an applicator, to shrink corneal tissue and apply the reshaping forces; or the cross-linking treatment system 100 applies a cross-linking agent, e.g., Riboflavin, and photoactivating light, e.g., UV light, to initiate cross-linking activity in selected areas of the cornea and apply the reshaping forces. The controller(s) 640 can determine the selected areas of the cornea for the incisions and the reshaping forces from the eye therapy system, such that the reshaping forces and the incisions combine to achieve a predetermined corrective reshaping of the cornea.

In the embodiments described herein, systems may include one or more controllers (e.g., a computer processing system that reads instructions on computer-readable storage media) to process the information determined for the anatomy of the eye, determine the locations, sizes, and depths for incisions to the corneal tissue, control the incision device in forming the incisions, and/or control the eye treatment systems in applying the eye treatment to the eye. Generally, the one or more controllers may be implemented as a combination of hardware and software elements. The hardware aspects may include combinations of operatively coupled hardware components including microprocessors, logical circuitry, communication/networking ports, digital filters, memory, or logical circuitry. The one or more controllers may be adapted to perform operations specified by a computer-executable code, which may be stored on a computer readable medium.

As described above, the one or more controllers may be a programmable processing device, such as an external conventional computer or an on-board field programmable gate array (FPGA) or digital signal processor (DSP) that executes software, or stored instructions. In general, physical processors and/or machines employed by embodiments for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment for performing all or a portion (if processing is distributed) of the processing performed in implementations. Computer code devices of exemplary embodiments can include any suitable interpretable or executable code mechanism, including but not limited to scripts, interpretable programs, dynamic link libraries (DLLs), Java classes and applets, complete executable programs, and the like. Moreover, parts of the processing of exemplary embodiments can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

Although embodiments have been described in connection with thermokeratoplasty, LASIK surgery, or the like, it is understood that the systems and methods described may be applied with other eye treatments.

Although the embodiments described above may employ Riboflavin as a cross-linking agent, it is understood that other substances may be employed as a cross-linking agent. Thus, for example Rose Bengal (4,5,6,7-tetrachloro-2',4',5',7'-tetraiodofluorescein) may be employed as cross-linking agent. Rose Bengal has been approved for application to the eye as a stain to identify damage to conjunctival and corneal cells. However, Rose Bengal can also initiate cross-linking activity within corneal collagen to stabilize the corneal tissue and improve its biomechanical strength Like Riboflavin, photoactivating light may be applied to initiate cross-linking activity by causing the Rose Bengal to form radicals and to convert $O_2$ in the corneal tissue into singlet oxygen. The photoactivating light may include, for example, UV light or green light.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

What is claimed is:

1. A system for treating an eye, comprising:
a first eye treatment system configured to apply reshaping forces to a cornea;
a second eye treatment system including a cutting instrument configured to form secondary incisions in selected regions of the cornea along layers of collagen fibrils in the selected regions to form slip planes parallel to a surface of the cornea that relieve stresses resulting from intraocular pressure associated with the reshaping forces applied by the first eye treatment system; and
a controller configured to determine the selected regions of the cornea for the secondary incisions formed by the cutting instrument of the second eye treatment system based on the reshaping forces applied by the first eye treatment system, the secondary incisions relieving the stresses associated with the reshaping forces, the reshaping forces and the secondary incisions combining to achieve a predetermined corrective reshaping of the cornea.

2. The system of claim 1, wherein the cutting instrument includes a femtosecond laser.

3. The system of claim 1, wherein the first eye treatment system includes a LASIK surgery system, the LASIK surgery system including a microkeratome that cuts a flap in the cornea and an excimer laser that ablates corneal tissue to apply the reshaping forces, the microkeratome and the excimer laser acting separately from the cutting instrument of the second eye treatment system, the secondary incisions formed by the cutting instrument being separate from the results of the actions of the microkeratome and the excimer laser.

4. The system of claim 1, wherein the first eye treatment system includes a thermokeratoplasty system, the thermokeratoplasty system including an applicator that applies energy to shrink corneal tissue and apply the reshaping forces.

5. The system of claim 1, wherein the first eye treatment system includes a cross-linking treatment system, the cross-linking treatment system including an applicator that applies a cross-linking agent to the cornea and a light source that provides photoactivating light for the cross-linking agent, the photoactivating light acting on the cross-linking agent initiating cross-linking activity in the selected regions to apply the reshaping forces.

6. The system of claim 5, wherein the cross-linking treatment system further comprises optical elements that direct the photoactivating light to the selected regions of the cornea with the applied cross-linking agent.

7. The system of claim 1, wherein the selected regions of the cornea for the secondary incisions determined by the controller include regions of posterior corneal tissue to relieve stress associated with the reshaping forces applied to the anterior corneal tissue.

8. A method for treating an eye, comprising:
applying, with a first eye treatment system, reshaping forces to a cornea;
forming, with a cutting instrument of a second eye treatment, secondary incisions in selected regions of the cornea along layers of collagen fibrils in the selected regions to form slip planes parallel to a surface of the cornea that relieve stresses resulting from intraocular pressure associated with the reshaping forces applied by the first eye treatment system; and
determining the selected regions of the cornea for the secondary incisions formed by the cutting instrument of the second eye treatment based on the reshaping forces applied by the first eye treatment system, the secondary incisions relieving the stresses associated with the reshaping forces, the reshaping forces and the secondary incisions combining to achieve a predetermined corrective reshaping of the cornea.

9. The method of claim 8 wherein the cutting instrument includes a femtosecond laser.

10. The method of claim 8 wherein the first eye treatment system includes a LASIK surgery system, the LASIK surgery system including a microkeratome and an excimer laser, wherein applying the reshaping forces includes ablating corneal tissue with the excimer laser after creating a corneal flap with the microkerotome, the microkeratome and the excimer laser acting separately from the cutting instrument of the second eye treatment system, the secondary incisions formed by the cutting instrument being separate from the results of the actions of the microkeratome and the excimer laser.

11. The method of claim 8 wherein the first eye treatment system includes a thermokeratoplasty system, the thermokeratoplasty system including an applicator, wherein applying the reshaping forces includes applying energy with the applicator to shrink corneal tissue.

12. The method of claim 8 wherein the first eye treatment system includes a cross-linking treatment system, the cross-linking treatment system including an applicator that applies a cross-linking agent to the cornea and a light source that provides photoactivating light for the cross-linking agent wherein applying the reshaping forces includes applying the cross-linking agent and directing the photoactivating light to the cross-linking agent in the selected regions to initiate cross-linking activity.

13. The method of claim 12 wherein the cross-linking treatment system further comprises optical elements that direct the photoactivating light to the selected regions of the cornea with the applied cross-linking agent.

14. The method of claim 8 wherein forming the secondary incisions includes forming the secondary incisions in posterior corneal tissue to relieve stress associated with the reshaping forces applied to the anterior corneal tissue.

15. A method for treating an eye, comprising:
applying a first treatment to an eye, the first treatment resulting in a requirement for post-procedural refractive correction of the cornea;
determining an amount of the refractive correction of the cornea to be achieved by cross-linking after the first treatment applied to the eye;
determining one or more doses of cross-linking agent and one or more corresponding doses of photoactivating light according to the determined amount of refractive correction of the cornea;
applying the one or more doses of cross-linking agent to the cornea; and
delivering, from a light source, the one or more doses of photoactivating light to the eye, the one or more doses of photoactivating light combining with the one or more doses of cross-linking agent to induce the determined amount of refractive correction of the cornea, the determined amount refractive correction of the cornea being induced without assistance of a mold applied to the eye during the delivery of the one or more doses of photoactivating light to the eye.

16. The method of claim 15 wherein the cross-linking agent includes Riboflavin, and the one or more doses of photoactivating light includes a dose of ultraviolet light greater than 5.4 $J/cm^2$.

17. The method of claim 15 wherein applying the first treatment to the eye includes conducting cataract surgery on the eye, the cataract surgery resulting in a residual myopia that requires the refractive correction of the cornea.

18. The method of claim 15 wherein applying the first treatment to the eye includes conducting LASIK surgery on the cornea, the LASIK surgery requiring additional reshaping of the cornea to achieve a desired corneal shape.

19. The method of claim 15 wherein applying the first treatment to the eye includes applying thermokeratoplasty to the cornea, the thermokeratoplasty requiring additional reshaping of the cornea to achieve a desired corneal shape.

20. The system of claim 1, wherein the secondary incisions at least partially disassociate or separate anterior corneal tissue from posterior corneal tissue in one or more of the selected regions.

21. The system of claim 1, wherein the second eye treatment system is configured to form the secondary incisions without ablation.

22. The method of claim 8, wherein the secondary incisions at least partially disassociate or separate anterior corneal tissue from posterior corneal tissue in one or more of the selected regions.

23. The method of claim 8, wherein the secondary incisions are formed after applying the first eye treatment system to reshape the cornea.

* * * * *